US012329686B2

(12) United States Patent
Kwen et al.

(10) Patent No.: US 12,329,686 B2
(45) Date of Patent: Jun. 17, 2025

(54) GOGGLES CAPABLE OF AUTOMATICALLY REMOVING INTERNAL MOISTURE

(71) Applicant: CNS COMPANY, Gwangju (KR)

(72) Inventors: Man Seong Kwen, Gwangju (KR); Se Eun Park, Gwangju (KR); Seung Hwan Yeo, Gwangju (KR)

(73) Assignee: CNS COMPANY, Gwangju (KR)

( * ) Notice: Subject to any disclaimer, the term of this patent is extended or adjusted under 35 U.S.C. 154(b) by 0 days.

(21) Appl. No.: 18/340,397

(22) Filed: Jun. 23, 2023

(65) Prior Publication Data

US 2024/0398624 A1 Dec. 5, 2024

(30) Foreign Application Priority Data

May 31, 2023 (KR) .................. 10-2023-0069700

(51) Int. Cl.
*A61F 9/02* (2006.01)

(52) U.S. Cl.
CPC .............. *A61F 9/029* (2013.01); *A61F 9/028* (2013.01)

(58) Field of Classification Search
CPC . A61F 9/02; A61F 9/026; A61F 9/028; G02C 11/08
See application file for complete search history.

(56) References Cited

U.S. PATENT DOCUMENTS 4,443,893 A * 4/1984 Yamamoto ............. G02C 11/08
2/436

* cited by examiner

*Primary Examiner* — Heather Mangine
*Assistant Examiner* — Erick I Lopez
(74) *Attorney, Agent, or Firm* — Finch & Maloney PLLC

(57) ABSTRACT

Provided are goggles which protect a user's face from external substances. The goggles may include a frame part coupled along an edge of a lens part and a moisture removal part detachably attached to the frame part, wherein the moisture removal part may automatically remove moisture inside the frame part by discharging the moisture inside the frame part to an outside.

10 Claims, 12 Drawing Sheets

GOGGLES CAPABLE OF AUTOMATICALLY REMOVING INTERNAL MOISTURE

CROSS-REFERENCE TO RELATED APPLICATION

This application claims the benefit of Republic of Korea Patent Application 10-2023-0069700 (filed 31 May 2023), the disclosure of which is hereby incorporated by reference herein.

BACKGROUND OF THE INVENTION

1. Field of the Invention

The present application relates to goggles which protect a user's face from external substances, and more specifically, to goggles which include a frame part coupled along an edge of a lens part and a moisture removal part detachably attached to the frame part, in which the moisture removal part automatically removes moisture inside the frame part by discharging the moisture inside the frame part from the outside.

2. Description of the Related Art

Generally, goggles are protective glasses, which are worn during outdoor leisure sports to protect the eyes from sunlight (ultraviolet rays and visible rays) and to prevent rain, wind, snow, dust, or the like from entering the eyes of a user, thereby protecting the field of view from being obstructed and preventing various safety accidents and infections of firefighters and quarantine medical personnel. Alternatively, goggles are mainly worn for medical purposes indoors and are used to prevent infections such as bacteria, SARS, MERS, and COVID-19.

Such goggles are composed of a lens and a frame supporting the lens, but the type and shape of the lens are varied depending on the purpose of use, such as riding, mountaineering, fishing, and the like. Specifically, in addition to the wind-breaking function, goggles used for riding are designed to come into close contact with the wearer's face because the goggles have to block foreign substances from entering the eyes. On the other hand, goggles used for mountaineering are designed to be well-ventilated because moisture is generated inside the lens and the frame when the goggles come into close contact with a facial part. In general, industrial goggles have a lens part formed on a front part thereof and a frame formed integrally with the lens or attachable to or detachable from the lens, and are worn by being fitted into the user's head.

Since the conventional goggles are composed of a hard frame for protecting the lens of the goggles, and the lens of the goggles is formed of a hard material, the weight of goggles itself is heavy and a considerable physical burden is imposed on the user when the goggles are worn for a long time. In particular, when the goggles are used for protection against COVID-19 or the like, users wear the goggles while wearing protective clothes to prevent infections, so that the goggles are filled with moisture due to a large amount of activity and breathing, resulting in difficulty in securing the field of view and difficulty in activity of users because the moisture enters the eyes.

SUMMARY OF THE INVENTION

One technical problem to be solved by the present application is to provide goggles capable of automatically removing internal moisture.

Another technical problem to be solved by the present application is to provide goggles which can selectively and automatically remove internal moisture because the goggles are detachably attached.

Still another technical problem to be solved by the present application is to provide goggles capable of automatically removing internal moisture, which has improved dehumidification efficiency.

Still another technical problem to be solved by the present application is to provide goggles capable of automatically removing internal moisture, which has improved convenience of user.

Still another technical problem to be solved by the present application is to provide goggles capable of automatically removing internal moisture, which has a light weight.

The technical problems to be solved by the present application are not limited to those described above.

In order to solve the technical problems, the present application provides goggles capable of automatically removing internal moisture.

According to one embodiment, the goggles capable of automatically removing internal moisture may include a lens part, a frame part coupled along an edge of the lens part, and a moisture removal part detachably attached to the frame part, wherein the moisture removal part may discharge moisture inside the frame from the outside.

According to one embodiment, the frame part may include: a front frame to which the lens part is coupled; a rear frame spaced apart from the front frame in a first direction directed to the user's face; a connection frame for connecting the front frame to the rear frame; and a first air ventilation part formed through an upper end of the connection frame, wherein the moisture removal part may be inserted into the first air ventilation part.

According to one embodiment, the moisture removal part may include: a first member to which a fan motor is coupled; a second member coupled to an upper end of the first member; and a third member coupled to an upper end of the second member, wherein the first member may include: a locking protrusion formed on a side surface of the first member so as to be coupled to the first air ventilation part; and a seating hole formed through a center of the first member so as to be connected to the first air ventilation part, and wherein the seating hole may be configured to be smaller than a cross section of the fan motor so as to fix the fan motor on the seating hole.

According to one embodiment, the second member may have an opening formed at a lower end of the second member, which is coupled to the first member, and a switch and a power supply part disposed at an upper end of the second member, which is coupled to the third member, and the switch and the power supply part may be electrically connected to the fan motor so that the moisture inside the frame part is discharged through the opening by rotation of the fan motor.

According to one embodiment, the frame part may further include a second air ventilation part formed through a lower end of the connection frame so that a moisture absorbent, which absorbs moisture from a lower end inside the frame part, is inserted into the second air ventilation part.

According to one embodiment, the frame part may further include a plurality of third air ventilation parts formed through an upper end of the rear frame so that air inside the frame part is naturally circulated.

According to the embodiment of the present application, goggles, which are worn on a user's face to protect the user's face from external substances, may include a lens part, a frame part coupled along an edge of the lens part, and a moisture removal part detachably attached to the frame part, wherein the moisture removal part may discharge moisture inside the frame part to an outside. Accordingly, the goggles can automatically remove the moisture inside the frame part, and can selectively and automatically remove the internal moisture because the goggles are detachably attached.

In addition, the frame part may include a front frame to which the lens part is coupled, a rear frame spaced apart from the front frame in a first direction directed to the user's face, a connection frame for connecting the front frame to the rear frame, and a first air ventilation part formed through an upper end of the connection frame, and may further include a second air ventilation part formed through a lower end of the connection frame so that a moisture absorbent, which absorbs moisture from a lower end inside the frame part, is inserted into the second air ventilation part, and a plurality of third air ventilation parts formed through an upper end of the rear frame. Accordingly, the moisture removal part may be inserted into the first air ventilation part, and the moisture absorbent for absorbing the moisture may be inserted into the second air ventilation part, so that internal air can be naturally circulated through the third air ventilation parts, thereby improving dehumidification efficiency.

In addition, the moisture removal part may include a first member to which a fan motor is coupled, a second member coupled to an upper end of the first member, and a third member coupled to an upper end of the second member, wherein the first member may include a locking protrusion formed on a side surface of the first member so as to be coupled to the first air ventilation part, and a seating hole formed through a center of the first member so as to be connected to the first air ventilation part, wherein the seating hole may be configured to be smaller than a cross section of the fan motor so as to fix the fan motor on the seating hole, and wherein the second member may have an opening formed at a lower end of the second member, which is coupled to the first member, and a switch and a power supply part disposed at an upper end of the second member, which is coupled to the third member, and wherein the switch and the power supply part may be electrically connected to the fan motor so that the moisture inside the frame part is discharged through the opening by rotation of the fan motor.

Accordingly, dehumidification efficiency can be improved, and convenience of user can be improved.

DETAILED DESCRIPTION OF THE INVENTION

Hereinafter, preferred embodiments of the present invention will be described in detail with reference to the accompanying drawings. However, the present invention may be embodied in different forms and should not be construed as limited to the embodiments set forth herein. Rather, the embodiments are provided so that this disclosure will be thorough and complete, and will fully convey the scope of the present invention to those skilled in the art.

In addition, it will be also understood that although the terms first, second, third, etc. may be used herein to describe various elements, these elements should not be limited by these terms. These terms are only used to distinguish one element from another element. Thus, a first element in some embodiments could be termed a second element in other embodiments without departing from the teachings of the present invention. Embodiments explained and illustrated herein include their complementary counterparts. As used herein, the term "and/or" includes any and all combinations of one or more of the associated listed elements.

The singular expression also includes the plural meaning as long as it does not differently mean in the context. In addition, the terms "comprise", "have" etc., of the description are used to indicate that there are features, numbers, steps, elements, or combination thereof, and they should not exclude the possibilities of combination or addition of one or more features, numbers, operations, elements, or a combination thereof. In addition, when detailed descriptions of related known functions or constitutions are considered to unnecessarily cloud the gist of the present invention in describing the present invention below, the detailed descriptions will not be included.

Figure 1:
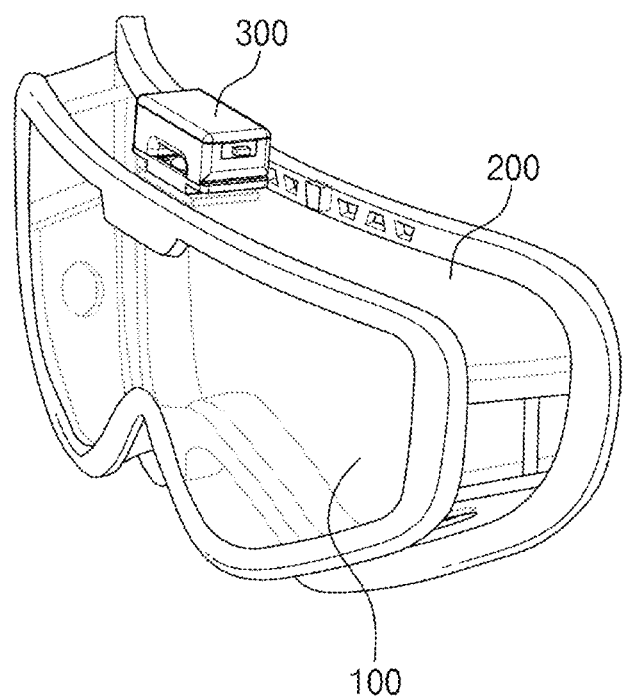
FIG. 1 is a perspective view for explaining goggles capable of automatically removing internal moisture according to an embodiment of the present application.
Figure 2:
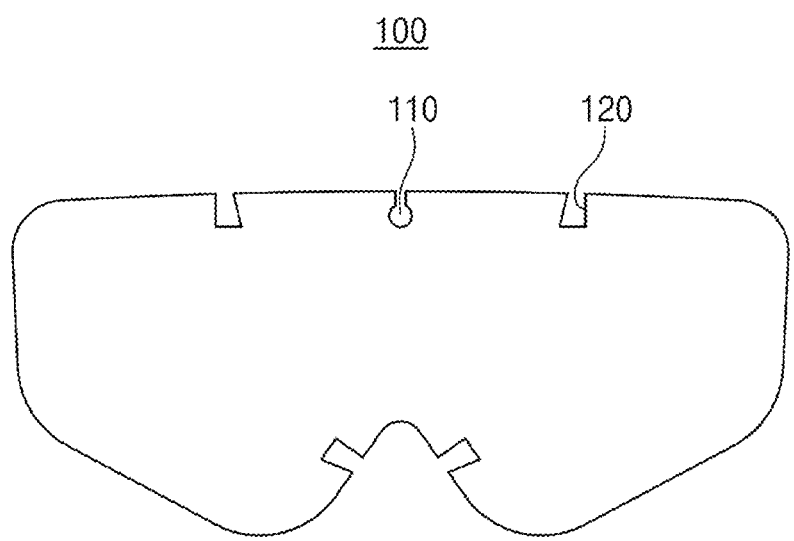
FIG. 2 is a view for explaining a lens part of the goggles capable of automatically removing internal moisture according to the embodiment of the present application.
Figure 3:
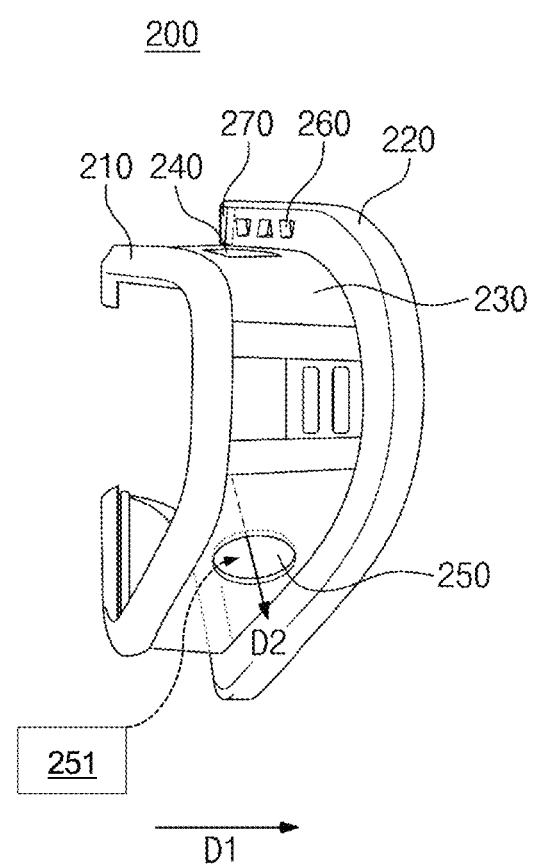
FIG. 3 is a side view for explaining a frame part of the goggles capable of automatically removing internal moisture according to the embodiment of the present application.
Figure 4A:
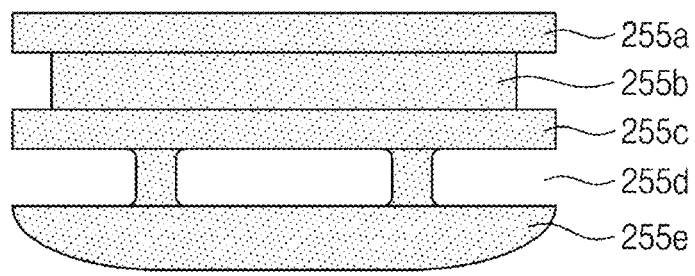
FIG. 4(a) is a front view for explaining an indirect air ventilation member inserted into the goggles capable of automatically removing internal moisture according to the embodiment of the present application.
Figure 4B:
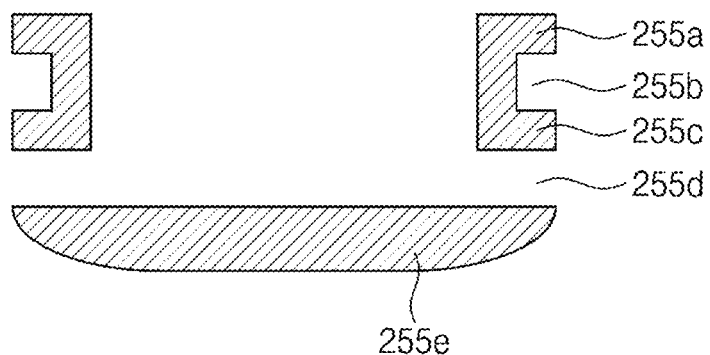
FIG. 4(b) is a sectional view for explaining the indirect air ventilation member inserted into the goggles capable of automatically removing internal moisture.
Figure 5:
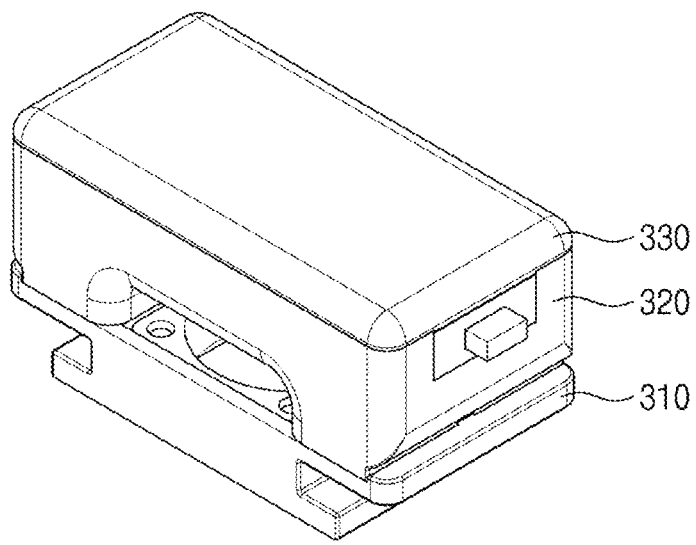
FIG. 5 is a perspective view for explaining a moisture removal part of the goggles capable of automatically removing internal moisture according to the embodiment of the present application.
Figure 6:
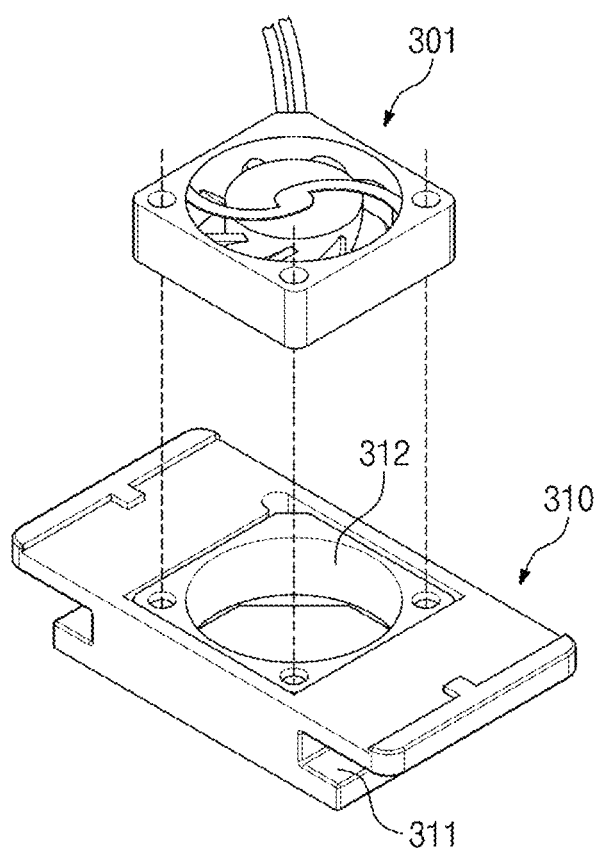
FIG. 6 is a view for explaining that a first member is coupled to a fan motor of the moisture removal part in the goggles capable of automatically removing internal moisture according to the embodiment of the present application.
Figure 7:
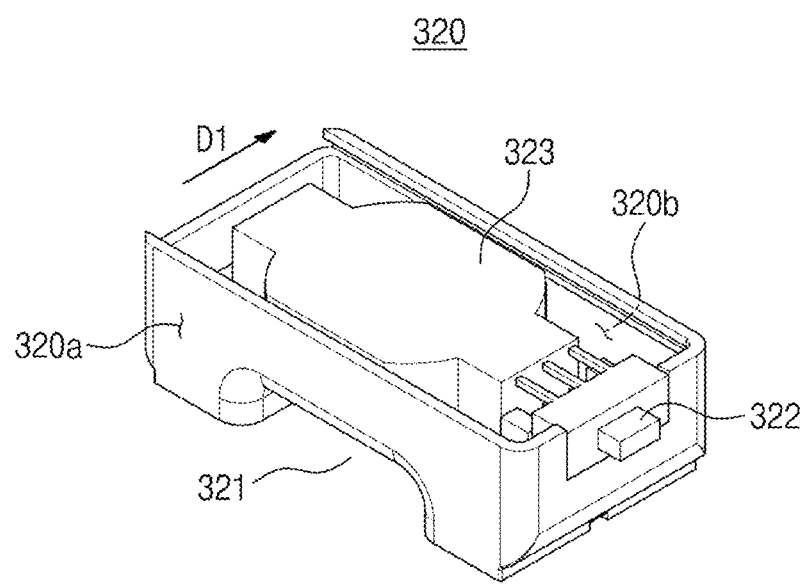
FIGS. 7 and 8 are views for explaining a second member of the moisture removal part in the goggles capable of automatically removing internal moisture according to the embodiment of the present application.
Figure 8:
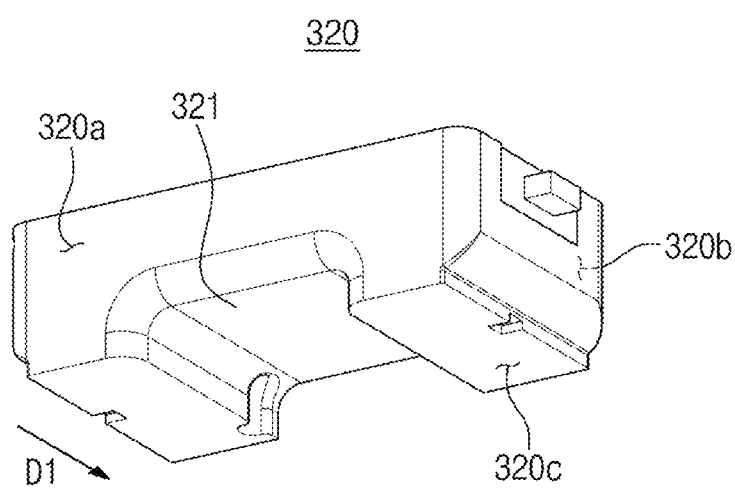

FIG. 1 is a perspective view for explaining goggles capable of automatically removing internal moisture according to an embodiment of the present application, FIG. 2 is a view for explaining a lens part of the goggles capable of automatically removing internal moisture according to the embodiment of the present application, FIG. 3 is a side view for explaining a frame part of the goggles capable of automatically removing internal moisture according to the embodiment of the present application, FIG. 4(a) is a front view for explaining an indirect air ventilation member inserted into the goggles capable of automatically removing internal moisture according to the embodiment of the present application, and FIG. 4(b) is a sectional view for explaining the indirect air ventilation member inserted into the goggles capable of automatically removing internal moisture, FIG. 5 is a perspective view for explaining a moisture removal part of the goggles capable of automatically removing internal moisture according to the embodiment of the present application, FIG. 6 is a view for explaining that a first member is coupled to a fan motor of the moisture removal part in the goggles capable of automatically removing internal moisture according to the embodiment of the present application, and FIGS. 7 and 8 are views for explaining a second member of the moisture removal part in the goggles capable of automatically removing internal moisture according to the embodiment of the present application.

Referring to FIGS. 1 to 8, goggles capable of automatically removing internal moisture according to an embodiment of the present application may include a lens part 100, a frame part 200, and a moisture removal part 300.

The lens part 100 may be coupled to the frame part 200. The lens part 100 may be formed of a transparent material to protect the user's face from external substances and secure the user's field of view. For example, the lens part 100 may be made of polycarbonate (PC) which is light, non-toxic, has high durability, and is resistant to low and high temperatures. Alternatively, the lens part 100 may be made of polyethylene terephthalate (PET). The lens part 100 may include a first coupling groove 110 and a second coupling groove 120.

The first coupling groove 110 is formed at the center of an upper end of the lens part 100 to be coupled to an upper end of the frame part 200. When the lens part 100 and the frame part 200 are coupled to each other, the first coupling groove 110 may be coupled to the frame part 200 prior to the second coupling groove 120. The first coupling groove 110 may be a circular concave groove.

A plurality of second coupling grooves 120 may be formed on the edge of the lens part 100. As described above, the second coupling groove 120 may be coupled later than the first coupling groove 110 when the lens part 100 and the frame part 200 are coupled to each other. The second coupling groove 120 may be a trapezoidal concave groove.

In other words, when the lens part 100 and the frame part 200 are coupled to each other, a position of the lens part 100 may be adjusted through the circular first coupling groove 110, and then the lens part 100 may be fixed to the frame part 200 through the trapezoidal second coupling groove 12. Accordingly, the lens part 100 and the frame part 200 may be easily and firmly coupled to each other.

The frame part 200 may be coupled to the edge of the lens part 100. The frame part 200 may include a curved surface so as to protect the user's face and secure the field of view. The frame part 200 may directly or indirectly make contact with the user's face. The frame part 200 may include a front frame 210, a rear frame 200, a connection frame 230, a first air ventilation part 240, a second air ventilation part 250, a third air ventilation part 260, and a support part 270.

The front frame 210 may be directly coupled to the lens part 100. The front frame 210 may include a curved surface so as to protect the user's face and secure the field of view.

The rear frame 220 may be spaced apart from the front frame 210 in a first direction D1 directed to the user's face. The rear frame 220 may include a curved surface so as to make contact with the user's face and secure the field of view. The rear frame 220 may be in direct contact with the user's face or may be in indirect contact with the user's face through a buffering member or the like.

The connection frame 230 may connect the front frame 210 and the rear frame 220. When a width of the connection frame 230, which is a distance between the front frame 210 and the rear frame 220, is greater than a distance between the user's eyes and glasses, the user may wear the goggles while wearing the glasses.

The front frame 210, the rear frame 220, and the connection frame 230 may be formed in one body.

The first air ventilation part 240 may be formed in the form of a through-hole that is formed through the upper end of the frame part 200 so that the moisture removal part 300 to be described later is inserted thereinto. In more detail, the first air ventilation part 240 may be formed through an upper end of the connection frame. The first air ventilation part 240 may include a shape profile corresponding to an outer surface of the moisture removal part 300. For example, the first air ventilation part 240 may have a rectangular shape.

The second air ventilation part 250 may be formed in the form of a through-hole that is formed through a lower end of the frame part 200 so that an indirect air ventilation member 255 to be described later is inserted thereinto. For example, the second air ventilation parts 250 may be formed through both sides of the lower end of the frame part 200, respectively, so as to be adjacent to both cheeks of the user. The second air ventilation part 250 may include an inclined surface for smooth detachable attachment of the indirect air ventilation member 255. The second air ventilation part 250 may include a cross section that is gradually narrowed from the inside of the goggles to the outside. According to one embodiment, and as illustrated in FIG. 3, the frame part 200 may further include a second air ventilation part 250 formed through a lower end of the connection frame 230 so that a moisture absorbent 251, which absorbs moisture from a lower end inside the frame part 200, is inserted into the second air ventilation part 250.

The indirect air ventilation member 255 may be detachably attached to the second air ventilation part 250 of the frame part 200. When the indirect air ventilation member 255 is attached to the second air ventilation part 250, the indirect air ventilation member 255 may be inserted into the second air ventilation part 250 in a second direction D2 directed to the outside from the inside of the goggles. In contrast, when the indirect air ventilation member 255 is detached from the second air ventilation part 250, the indirect air ventilation member 255 may be detached in a direction opposite to the second direction D2. The indirect air ventilation member 255 may extend in the second direction D2, and may have an open upper end and a hollow cylindrical shape. The indirect air ventilation member 255 may include a first protruding part 255a, a recessed part 255b, a second protruding part 255c, an air ventilation hole 255d, and a closing part 255e.

The first protruding part 255a may protrude from the open upper end of the indirect air ventilation member 255 in an outer circumferential direction.

The recessed part 255b may be recessed at a lower end of the first protruding part 255a in an inner circumferential direction of the cylinder.

The second protruding part 255c may protrude from a lower end of the recessed part 255b in the outer circumferential direction of the cylinder.

The air ventilation hole 255d may be formed through a lower end of the second protruding part 255c in a circumferential direction. A plurality of air ventilation holes 255d may be provided.

The closing part 255e may be perpendicular to the second direction D2. The closing part 255e may be formed at a lower end of the air ventilation hole 255d. The closing part 255e may be configured to block the air ventilation hole 255d.

The third air ventilation part 260 may be formed through the upper end of the frame part 200. For example, the third air ventilation part 260 may be formed with a plurality of through-holes to connect the inside and the outside of the upper end of the goggles. As shown in FIG. 1, a plurality of third air ventilation parts 260 may be formed along the upper end of the frame part 200 to improve air circulation efficiency.

In other words, the moisture removal part 300 may be inserted through the first air ventilation part 240 to automatically discharge the moisture inside the frame part 200, the indirect air ventilation member 255 may be inserted through the second air ventilation part 250 to indirectly discharge the moisture inside the frame part 200, and air inside the frame part 200 may be naturally circulated through the third air ventilation part 260. Accordingly, the moisture inside the frame part 200 may be automatically removed, and dehumidification efficiency may thus be improved, thereby improving convenience of user.

The support part 270 may be disposed between the plurality of third air ventilation parts 260 in the rear frame 220. The support part 270 may prevent the rear frame 220 on which the air ventilation parts 260 are located from being bent or damaged.

The moisture removal part 300 may discharge the moisture inside the frame part 200 to the outside. As described above, the moisture removal part 300 may be detachably attached to the first air ventilation part 240. The moisture removal part 300 may include a fan motor 301, a first member 310, a second member 320, and a third member 330.

The fan motor 301 may be coupled to the first member 310 to be described later. For example, the fan motor 301 may include a screw hole and may be coupled to the first member 310 through a screw. The fan motor 301 may include a rotating blade to transfer the moisture inside the frame part 200 to the outside of the frame part 200.

The first member 310 may be fixed to the first air ventilation part 240. The first member 310 may include a locking protrusion 311, a seating hole 312, and a screw hole.

The locking protrusion 311 may be recessed at a side surface of the first member 310 so as to come into close contact with an inner surface of the first air ventilation part 240.

The seating hole 312 may be formed through the center of the first member 310 so as to be connected to the first air ventilation part 240. The seating hole 312 may be configured to be smaller than a cross section of the fan motor 301.

As described above, the first member 310 may be firmly coupled to the fan motor 301 by inserting screws into the screw hole of the first member 310 and the screw hole of the fan motor 301.

In other words, the fan motor 301 is larger than the seating hole 312, and accordingly, the fan motor 301 is fixed on the seating hole 312 without falling into the seating hole 312, and the fan motor 301 may be coupled to the first member 310 through the screw holes and the screws. Therefore, the fan motor 301 may be firmly fixed to the frame part 200 to stably remove the moisture inside the frame part 200.

The second member 320 may be coupled to the upper end of the first member 310. The second member 320 may have a hexahedral shape including a first surface 320a, a second surface 320b, and a third surface 320c. The second member 320 may include an opening 321, a switch 322, and a power supply part 323.

The first surface 320a may be defined as a rear surface of the second member 320, which faces the user's face.

The second surface 320b may be defined as a front surface of the second member 320, which is opposite to the first surface 320a.

The third surface 330c may be defined as a lower end surface of the second member 320, which is in contact with the frame part 200.

The opening 321 may communicate with the first air ventilation part 240 of the frame part 200 through the fan motor 301. The opening 321 may be formed through a lower end of the second member 320, which is coupled to the first member 310, in the first direction D1. In more detail, the opening 321 may be formed from the second surface 320b of the second member 320, which is the front surface of the second member 320, to the first surface 320a, which is the rear surface of the second member 320, and at least a portion of the third surface 330c, which is the lower end surface of the second member 320, may be open.

In other words, the opening 321 may be formed in the first direction D1 directed to the user's face from the front frame to discharge the moisture inside the frame part 200 in the first direction D1 and/or a direction opposite to the first direction D1. As a result, the moisture inside the frame part 200 may be quickly discharged through the opening 321, so that the dehumidification efficiency may be improved.

The switch 322 may be disposed inside the second member 320 to selectively connect the fan motor 301 to the power supply part 323.

The power supply part 323 may be disposed inside the second member 320 to supply power to the fan motor 302. The power supply part 323 may include a battery, a solar cell, or the like, but is not limited thereto.

The third member 330 may be coupled to an upper end of the second member 320 to protect the first member 310 and the second member 320.

Figure 9:
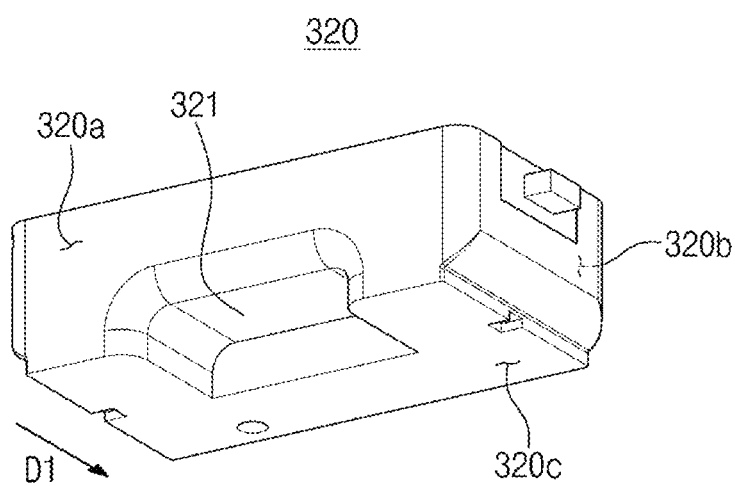
FIG. 9 is a view for explaining an opening of the second member of the moisture removal part in the goggles capable of automatically removing internal moisture according to a first modification of the present application.

FIG. 9 is a view for explaining an opening of the second member of the moisture removal part in the goggles capable of automatically removing internal moisture according to a first modification of the present application.

Referring to FIG. 9, goggles capable of automatically removing internal moisture according to a first modification of the present application may include a lens part 100, a frame part 200, and a moisture removal part 300 including a fan motor 301, a first member 310, a second member 320, and a third member 330.

Since the first lens part 100, the frame part 200, the fan motor 301, the first member 310, and the third member 330 according to the first modification of the present application are substantially the same as the lens part 100, the frame part 200, the fan motor 301, the first member 310, and the third member 330 according to the embodiment of the present application, detailed descriptions thereof will be omitted.

The second member 320 according to the first modification of the present application may be coupled to an upper end of the first member 310. The second member 320 may have a hexahedral shape including a first surface 320a, a second surface 320b, and a third surface 320c. The second member 320 may include an opening 321 in which at least a portion of the second member 320 is open.

The first surface 320a may be defined as the rear surface of the second member 320, which faces the user's face.

The second surface 320b may be defined as a front surface of the second member 320, which is opposite to the first surface 320a.

The third surface 330c may be defined as a lower end surface of the second member 320, which is in contact with the frame part 200.

The opening 321 may communicate with the first air ventilation part 240 of the frame part 200 through the fan motor 301. The opening 321 may be formed through a lower end of the second member 320, which is coupled to the first member 310, in the first direction D1 directed to the user's face from the front frame 210. In more detail, the opening 321 may be formed from the second surface 320b, which is the front surface of the second member 320, to the first surface 320a, which is the rear surface of the second surface 320b. That is, the opening 321 may not be formed on the first surface 320a, which is the rear surface of the second member 320, may extend from the second surface 320b, which is the front surface of the second member 320, and may include an end surface on which the opening 321 ends, and at least a portion of the third surface 330c, which is the lower end surface of the second member 320, may be open.

In other words, the opening 321 may be formed in a direction opposite to the first direction D1, which is directed to the front frame 210 from the user's face, to discharge the moisture inside the frame part 200 in the direction opposite to the first direction D1. As a result, the moisture inside the frame part 200 may be discharged only in a direction opposite to the user's face, not in the direction toward the user's face, thereby improving convenience of user.

Figure 10:
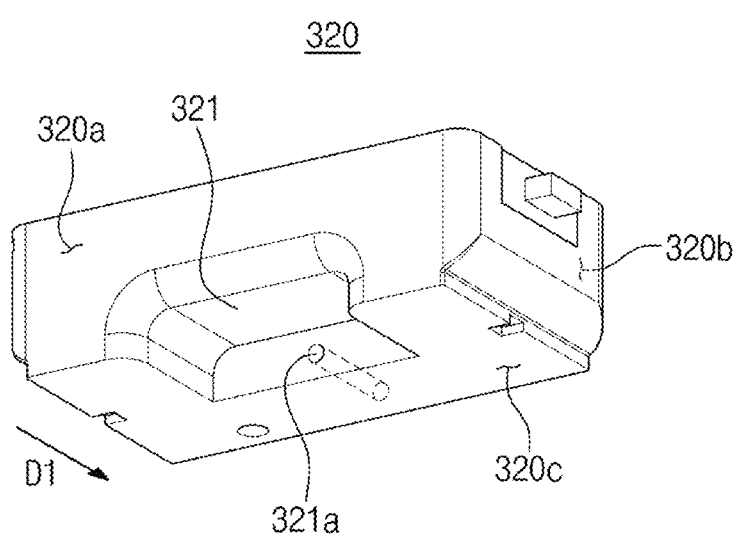
FIG. 10 is a view for explaining an opening of the second member of the moisture removal part in the goggles capable of automatically removing internal moisture according to a second modification of the present application.

FIG. 10 is a view for explaining an opening of the second member of the moisture removal part in the goggles capable of automatically removing internal moisture according to a second modification of the present application.

Referring to FIG. 10, goggles capable of automatically removing internal moisture according to a second modification of the present application may include a lens part 100, a frame part 200, and a moisture removal part 300 including a fan motor 301, a first member 310, a second member 320, and a third member 330.

Since the first lens part 100, the frame part 200, the fan motor 301, the first member 310, and the third member 330 according to the second modification of the present application are substantially the same as the lens part 100, the frame part 200, the fan motor 301, the first member 310, and the third member 330 according to the embodiment of the present application, detailed descriptions thereof will be omitted.

The second member 320 according to the second modification of the present application may be coupled to an upper end of the first member 310. The second member 320 may have a hexahedral shape including a first surface 320a, a second surface 320b, and a third surface 320c. The second member 320 may include an opening 321 and a circulation hole 321a.

The first surface 320a may be defined as the rear surface of the second member 320, which faces the user's face.

The second surface 320b may be defined as a front surface of the second member 320, which is opposite to the first surface 320a.

The third surface 330c may be defined as a lower end surface of the second member 320, which is in contact with the frame part 200.

The opening 321 may communicate with the first air ventilation part 240 of the frame part 200 through the fan motor 301. The opening 321 may be formed through a lower end of the second member 320, which is coupled to the first member 310, in the first direction D1 directed to the user's face from the front frame 210, and may not be formed through the first surface 320a, which is the rear surface of the second member 320. That is, the opening 321 may not be formed on the first surface 320a, which is the rear surface of the second member 320, may extend from the second surface 320b, which is the front surface of the second member 320, and may include an end surface on which the opening 321 ends, and at least a portion of the third surface 330c, which is the lower end surface of the second member 320, may be open.

The seating hole 321a may be formed from the end surface on which the opening 321 ends to the first surface 320a, which is the rear surface of the second member 320. The size of the seating hole 321a may be smaller than the size of the opening 321. That is, during discharge of the moisture inside the frame part 200, an amount of moisture discharged through the opening 321 may be relatively greater than an amount of moisture discharged through the seating hole 321a.

In other words, the opening 321 may be formed in a direction opposite to the first direction D1, which is directed to the front frame 210 from the user's face, to discharge a relatively large amount of moisture in the direction opposite to the first direction D1. Meanwhile, the seating hole 321a may be formed in the first direction D1 directed to the user's face from the front frame 210 to discharge a relatively small amount of moisture in the first direction D1, thereby assisting air circulation. As a result, most of the moisture inside the frame part 200 may be discharged in a direction opposite to the user's face, not in the direction toward the user's face, through the opening 321, so that air circulation inside the frame part 200 may be assisted through the seating hole 321a, thereby increasing moisture removal efficiency and improving convenience for user's breathing.

Figure 11:
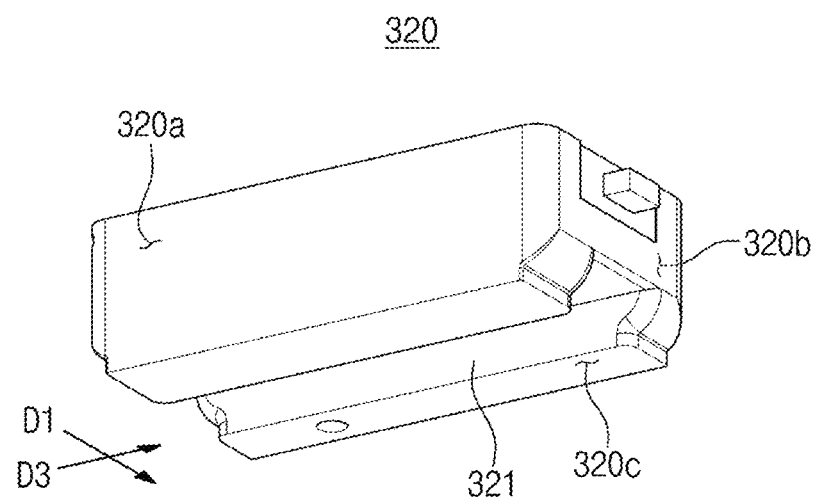
FIG. 11 is a view for explaining an opening of the second member of the moisture removal part in the goggles capable of automatically removing internal moisture according to a third modification of the present application.

FIG. 11 is a view for explaining an opening of the second member of the moisture removal part in the goggles capable of automatically removing internal moisture according to a third modification of the present application.

Referring to FIG. 11, the goggles capable of automatically removing internal moisture according to a third modification of the present application may include a lens part 100, a frame part 200, and a moisture removal part 300 including a fan motor 301, a first member 310, a second member 320, and a third member 330.

Since the first lens part 100, the frame part 200, the fan motor 301, the first member 310, and the third member 330 according to the third modification of the present application are substantially the same as the lens part 100, the frame part 200, the fan motor 301, the first member 310, and the third member 330 according to the embodiment of the present application, detailed descriptions thereof will be omitted.

The second member 320 according to the third modification of the present application may be coupled to an upper end of the first member 310. The second member 320 may have a hexahedral shape. The second member 320 may include an opening 321 in which at least a portion of the second member 320 is open.

The opening 321 may communicate with the first air ventilation part 240 of the frame part 200 through the fan motor 301. The opening 321 may be formed through a lower end of the second member 320, which is coupled to the first member 310, in a third direction D3 perpendicular to the first direction D1 directed to the user's face from the front frame 210. In more detail, the opening 321 may be formed through both side surfaces of the second member 320.

In other words, the opening 321 may be formed in the third direction D3 perpendicular to the first direction D1 directed to the user's face to discharge the moisture inside the frame part 200 in the third direction D3. As a result, the moisture inside the frame part 200 may be discharged only in a direction perpendicular to the direction toward the user's face through the opening 321 formed in the third direction D3, thereby improving convenience of user.

Figure 12:
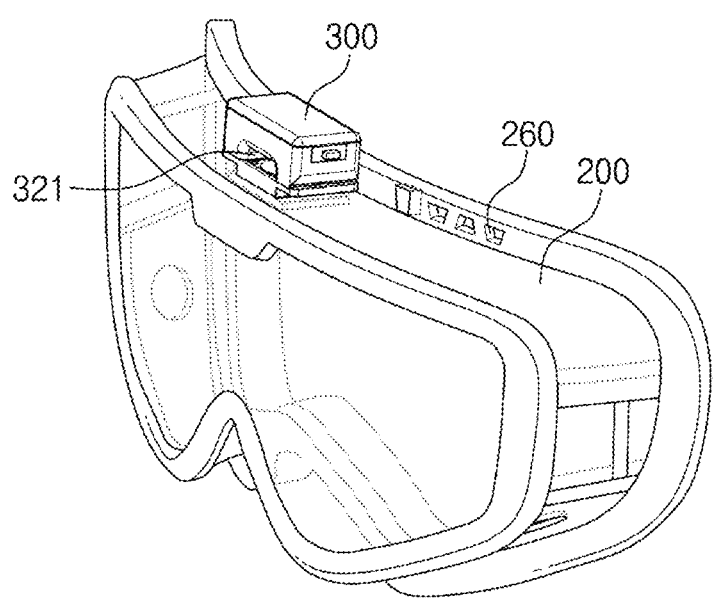
FIG. 12 is a view for explaining a third air ventilation part of the frame part in the goggles capable of automatically removing internal moisture according to a fourth modification of the present application.

FIG. 12 is a view for explaining a third air ventilation part of the frame part in the goggles capable of automatically removing internal moisture according to a fourth modification of the present application.

Referring to FIG. 12, a third air ventilation part 260 according to a fourth modification of the embodiment of the present application may be formed through an upper end of the frame part 200. For example, the third air ventilation part 260 may be formed with a plurality of through-holes to connect the inside and the outside of the upper end of the goggles. A plurality of third air ventilation parts 260 may be formed along the upper end of the frame part 200, and may not be formed around the moisture removal part 300. That is, air inside the frame part 200 may be naturally circulated through the plurality of third air ventilation parts 260, and simultaneously, the moisture discharged from the moisture removal part 300 may be prevented from entering the frame part 200 again through the third air ventilation parts 260, thereby improving air circulation efficiency.

While the present invention has been described in connection with the embodiments, it is not to be limited thereto but will be defined by the appended claims. In addition, it is to be understood that those skilled in the art can substitute, change or modify the embodiments in various forms without departing from the scope and spirit of the present invention.

What is claimed is:

1. Goggles capable of automatically removing internal moisture, which are configured to be worn on a user's face to protect the user's face from external substances, the goggles comprising:
a lens part;
a frame part coupled along an edge of the lens part, the frame part including:
a front frame to which the lens part is coupled,
a rear frame that is spaced apart from the front frame and that is configured to be in a first direction directed to the user's face,
a connection frame that connects the front frame to the rear frame, and
a first air ventilation part formed through an upper end of the connection frame; and
a moisture removal part detachably attached to the frame part, and inserted into the first air ventilation part of the frame part, the moisture removal part including:
a first member to which a fan motor is coupled,
a second member, and
a third member coupled to an upper end of the second member,
wherein the moisture removal part is configured to discharge moisture inside the frame part to outside the frame part,
wherein a lower end of the second member has an opening formed therein,
wherein the lower end of the second member is coupled to an upper end of the first member
wherein the second member has a switch and a power supply part disposed at an upper end of the second member, and
wherein the switch and the power supply part are electrically connected to the fan motor so that moisture inside the frame part is discharged through the opening by rotation of the fan motor.

2. The goggles of claim 1, wherein the frame part further includes:
a second air ventilation part formed through a lower end of the connection frame, the second air ventilation part configured to receive a moisture absorbent configured to absorb moisture from inside the frame part.

3. The goggles of claim 2, wherein the frame part further includes:
a plurality of third air ventilation parts formed through an upper end of the rear frame so that air inside the frame part is naturally circulated.

4. Goggles comprising:
a lens part;
a frame part coupled to the lens part, the frame part including:
a front frame to which the lens part is coupled,
a rear frame spaced apart from the front frame and configured to be toward a user's face,
a connection frame that connects the front frame to the rear frame, and
a first air ventilation part formed through an upper end of the connection frame; and
a moisture removal part detachably attached to the frame part, and inserted into the first air ventilation part of the frame part, the moisture removal part including:
a first member to which a fan and a fan motor is coupled, the fan motor configured to rotate the fan,
a second member, and
a third member coupled to an upper end of the second member,
wherein a lower end of the second member has an opening formed therein,
wherein the lower end of the second member is coupled to an upper end of the first member,
wherein the second member has a switch and a power supply part disposed at an upper end of the second member, and
wherein the switch and the power supply part are electrically connected to the fan motor so that moisture inside the frame part is discharged through the opening by rotation of the fan.

5. The goggles of claim 4, wherein the frame part further includes a second air ventilation part formed through a lower end of the connection frame, the second air ventilation part configured to receive a moisture absorbent configured to absorb moisture from inside the frame part.

6. The goggles of claim 4, wherein the frame part further includes a plurality of second air ventilation parts formed through an upper end of the rear frame so that air inside the frame part is naturally circulated.

7. Goggles comprising:
a lens part;

a frame part coupled to the lens part, the frame part including:
- a front frame to which the lens part is coupled,
- a rear frame spaced apart from the front frame and configured to be toward a user's face, and
- a connection frame that connects the front frame to the rear frame; and a moisture removal part detachably attached to the frame part, the moisture removal part including:
- a first member to which a fan and a fan motor is coupled,
- a second member, and
- a third member coupled to an upper end of the second member, wherein the fan motor is configured to rotate the fan, wherein a lower end of the second member is coupled to an upper end of the first member, and has an opening formed therein, wherein an upper end of the second member has a switch and a power supply part disposed thereon, and wherein the switch and the power supply part are electrically connected to the fan motor so that moisture inside the frame part is discharged through the opening by rotation of the fan.

8. The goggles of claim 7, further comprising an air ventilation part formed through an upper end of the connection frame, the air ventilation part configured to receive the moisture removal part therein.

9. The goggles of claim 7, further comprising an air ventilation part formed through a lower end of the connection frame, the air ventilation part configured to receive a moisture absorbent configured to absorb moisture from inside the frame part.

10. The goggles of claim 7, further comprising a plurality of air ventilation parts formed through an upper end of the rear frame so that air inside the frame part is naturally circulated.

* * * * *